United States Patent [19]
Reidy

[11] Patent Number: 5,366,705
[45] Date of Patent: Nov. 22, 1994

[54] GRAVITY FEED ULTRAVIOLET LIQUID STERILIZATION SYSTEM

[75] Inventor: James J. Reidy, 1260 Main St., Holden, Mass. 01520-1020

[73] Assignee: James J. Reidy, Holden, Mass.

[21] Appl. No.: 73,948

[22] Filed: Jun. 8, 1993

[51] Int. Cl.$^5$ ............................................. A61L 2/10
[52] U.S. Cl. ........................ 422/243; 422/186.3; 422/405; 422/24; 250/434; 250/437; 210/243; 210/748
[58] Field of Search ............... 422/22, 24, 243, 186.3, 422/905; 250/432 R, 434, 437, 438; 210/192, 143, 748

[56] References Cited

U.S. PATENT DOCUMENTS

| | | | |
|---|---|---|---|
| 1,193,143 | 8/1916 | Helnronner et al. | 250/437 |
| 2,167,233 | 7/1939 | Dorcas | 250/434 |
| 3,433,946 | 3/1969 | Hardwick | 250/372 |
| 3,485,576 | 12/1969 | McRae et al. | 422/24 |
| 3,562,520 | 2/1971 | Hippen | 250/372 |
| 3,750,370 | 8/1973 | Brauss et al. | 96/140 |
| 3,837,800 | 9/1974 | Wood | 422/24 |
| 3,923,663 | 12/1975 | Reid | 210/251 |
| 3,971,947 | 7/1976 | Lambert et al. | 422/24 |
| 4,017,735 | 4/1977 | Siegel | 422/24 |
| 4,273,660 | 6/1981 | Beitzel | 422/24 |
| 4,274,970 | 6/1981 | Beitzel | 422/24 |
| 4,367,410 | 1/1983 | Wood | 422/24 |
| 4,400,270 | 8/1983 | Hillman | 422/24 |
| 4,467,206 | 8/1984 | Taylor et al. | 422/24 |
| 4,615,799 | 10/1986 | Mortensen | 422/24 |
| 4,757,205 | 7/1988 | Latel et al. | 422/24 |
| 4,757,921 | 7/1988 | Snowball | 422/24 |
| 4,762,613 | 8/1988 | Snowball | 422/24 |
| 4,767,932 | 8/1988 | Ellner | 422/24 |
| 4,769,131 | 9/1988 | Noll et al. | 210/85 |
| 4,798,702 | 1/1989 | Tucker | 210/748 |
| 4,857,204 | 8/1989 | Joklik | 210/695 |
| 4,909,931 | 3/1990 | Bibi | 210/85 |
| 4,968,437 | 11/1990 | Noll et al. | 210/748 |
| 4,968,891 | 11/1990 | Shawar et al. | 250/438 |
| 4,971,687 | 11/1990 | Anderson | 210/85 |
| 5,006,244 | 4/1991 | Maarschalkerwerrd | 210/243 |
| 5,026,477 | 6/1991 | Yen | 210/169 |
| 5,037,618 | 8/1991 | Hager | 422/186.03 |
| 5,069,782 | 12/1991 | Moyher, Jr. et al. | 210/192 |
| 5,078,876 | 1/1992 | Whittier et al. | 210/315 |
| 5,151,252 | 9/1992 | Moss | 422/186.3 |

*Primary Examiner*—Robert J. Warden
*Assistant Examiner*—T. A. Trembley
*Attorney, Agent, or Firm*—Brian M. Dingman

[57] ABSTRACT

An ultraviolet liquid sterilization system including an ultraviolet light source. Provision is made for gravity feeding a liquid to be sterilized past the ultraviolet light source to expose the liquid immediately to the light to sterilize the liquid without the need for a pump, or pressure.

8 Claims, 3 Drawing Sheets

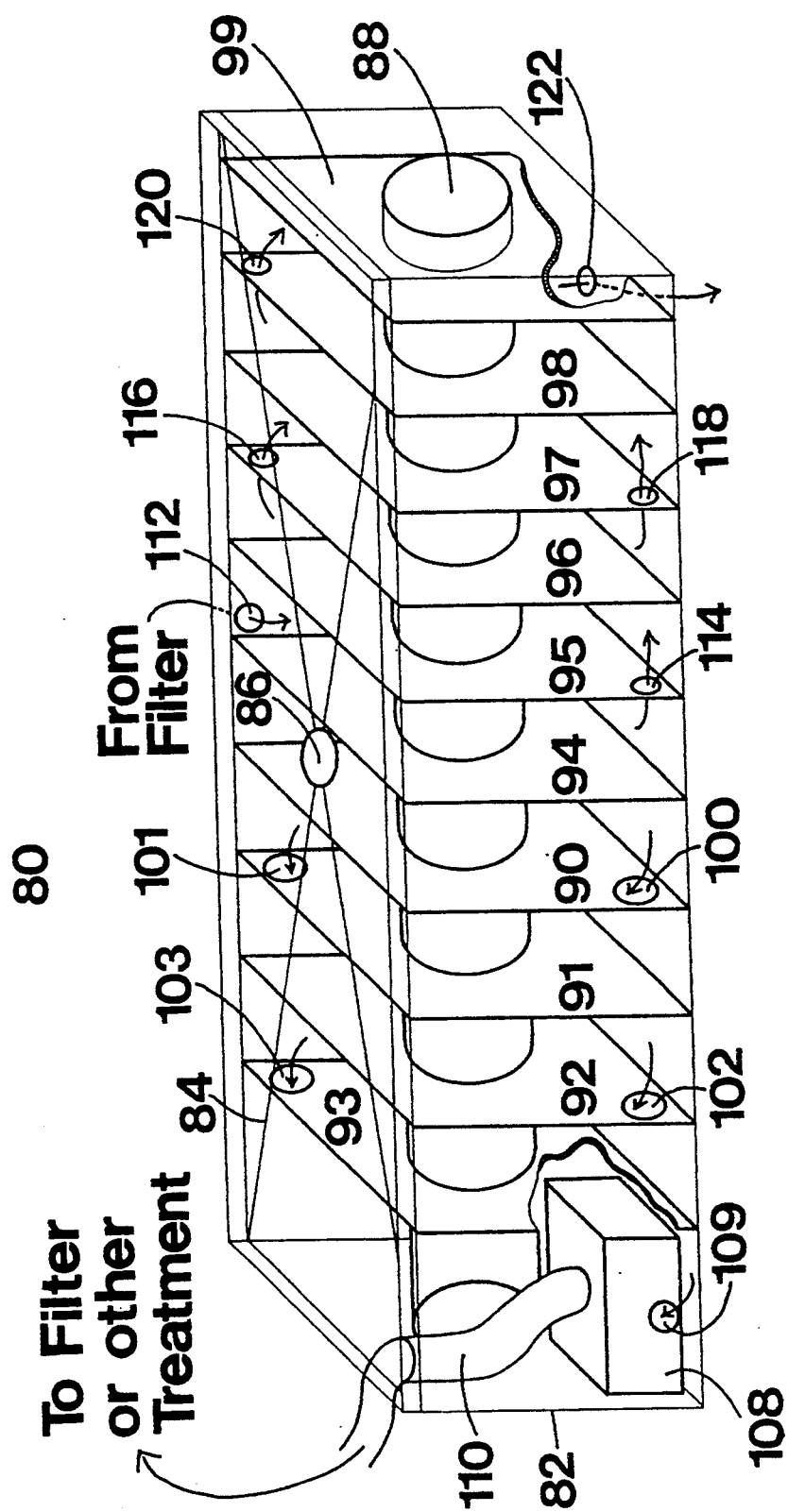

GRAVITY FEED ULTRAVIOLET LIQUID STERILIZATION SYSTEM

FIELD OF INVENTION

This invention relates to an ultraviolet liquid sterilization system that gravity-feeds a liquid past an ultraviolet light source so that the device can operate without a pump upstream of the sterilization system.

BACKGROUND OF INVENTION

It is well known that ultraviolet light in the proper dose kills most bacteria, algae, viruses, mold spores, and other microorganisms found in liquids such as water. There have been many ultraviolet water sterilization systems proposed to take advantage of this phenomenon. U.S. Pat. Nos. 4,769,131 and 4,968,437 issued to Noll et al. disclose an ultraviolet purification system in which water is pumped through tubes helically coiled around an ultraviolet lamp to provide maximum ultraviolet exposure time for a given tube length to create a relatively compact sterilization system for potable water.

This system as well as other known systems suffer from a number of drawbacks which make them less than ideal solutions to the water purification problem.

On problem common to these systems is that the liquid must be pumped under pressure past the ultraviolet lamp both before and after filtration. This requires a relatively large pump that draws a relatively great amount of power. In addition, such systems are typically designed to treat tap water, and are incapable of taking water from another source such as collecting water dripping off a condensing coil of a dehumidification or air conditioning system.

SUMMARY OF INVENTION

It is therefore an object of this invention to provide an ultraviolet liquid sterilization system that allows liquid to be gravity fed by the ultraviolet light source.

It is a further object of this invention to provide such a system that uses less power than other such systems.

It is a further object of this invention to provide such a system that is extremely compact.

It is a further object of this invention to provide such a system that can efficiently sterilize small amounts of water.

This invention results from the realization that sterilization of potable water and other liquids may be accomplished by providing an ultraviolet light source and gravity feeding the liquid to be sterilized past the ultraviolet light source to sterilize the liquid before it reaches any pump required in the liquid distribution system.

This invention features an ultraviolet liquid sterilization system which includes an ultraviolet light source and means for gravity feeding a liquid to be sterilized past the ultraviolet light source to expose the liquid to the light to sterilize the liquid.

In one embodiment, the means for gravity feeding the liquid may include a tube which preferably follows a sinuous path to increase the liquid light exposure time. The path preferably includes at least one elongated almost horizontal section to slow liquid flow and thereby further increase the liquid light exposure time. The tube inlet and outlet are preferably both in a direct light path to the ultraviolet light source to create a sterile liquid entrance and exit, respectively.

The system may further include means for passing the liquid by the ultraviolet light source a second time, in one embodiment downstream of a filter and/or other treatment means. The system may further include an enclosure housing the ultraviolet light source and the tube. In that case, there may further be included one or more partitions in the enclosure for supporting tile tube and the ultraviolet light source. In one embodiment there are a plurality of spaced partitions each having a hole for passing the ultraviolet light source and the tube. The enclosure top may be a drip pan or a collection pan for catching water and funneling it into the tube.

In an alternative embodiment, the means for gravity feeding the liquid may include a series of chambers that are in fluid communication. The chambers may be formed in an enclosure by baffle plates creating a series of adjacent chambers. In that case, the baffle plates may include openings arranged toward opposite edges of adjacent plates to create a tortuous liquid flow path. The enclosure may include a second series of chambers for feeding the liquid past the ultraviolet light source a second time. This second series of chambers may be formed as well by baffle plates creating a series of adjacent chambers in which the baffle plates include openings arranged toward opposite edges of adjacent plates to create a tortuous liquid flow path. The inside of the enclosure may be coated with a UV reflective or protective coating. The chamber may include a sterile liquid inlet and outlet directly exposed to the ultraviolet light.

There may further be included a pump for transferring liquid from a chamber, and a liquid filter or treatment system downstream of the pump. The baffle plates may include a central opening for accepting the ultraviolet light source.

In a more specific embodiment, the ultraviolet liquid sterilization system includes an ultraviolet lamp, a tube having an inlet exposed to light from the lamp and bent along a sinuous path along a side of the lamp, in which the path includes an elongated almost horizontal section to slow liquid flow and thereby further increase the liquid light exposure time. Further included in this embodiment is an enclosure for housing the lamp and the tube in which the enclosure includes a series of partitions having openings for supporting the lamp and the tube. Finally, this embodiment includes a sloped enclosure top for collecting liquid and directing it to an opening communicating with the tube inlet for directing liquid into the tube past the ultraviolet lamp.

In another alternative embodiment, the ultraviolet liquid sterilization system of this invention includes an ultraviolet lamp, an enclosure for housing the lamp, a series of space baffle plates in the enclosure dividing the enclosure into a series of adjacent chambers, the baffle plates each including a central opening for supporting the lamp passing therethrough. Further included is an opening at the enclosure top for allowing liquid to enter the first in a series of chambers, an opening through the lower side of the baffle plate adjacent the first chamber to pass liquid to the second chamber, and an opening through the upper side of the baffle plate adjacent the second chamber to pass the liquid out of the second chamber, the baffle plates and openings creating a tortuous liquid flow path past the lamp to increase the liquid light exposure time for greater sterility.

BRIEF DESCRIPTION OF THE DRAWINGS

Other objects, features and advantages will occur to those skilled in the art from the following description of preferred embodiments and the accompanying drawings in which:

FIG. 3 is a partly cross sectional axonometric view of an alternative to the system of FIG. 1.

DISCLOSURE OF PREFERRED EMBODIMENTS

This invention may be accomplished in an ultraviolet liquid sterilization system that includes an ultraviolet light source such as an ultraviolet lamp along with various means for gravity feeding a liquid such as water to be sterilized past the ultraviolet light source in a first exposure just after collection in order to immediately sterilize the liquid. The system may further include an optional second pass past the ultraviolet light source downstream of a filter to further ensure that the water exiting the unit is both clean and sterile.

Figure 1:
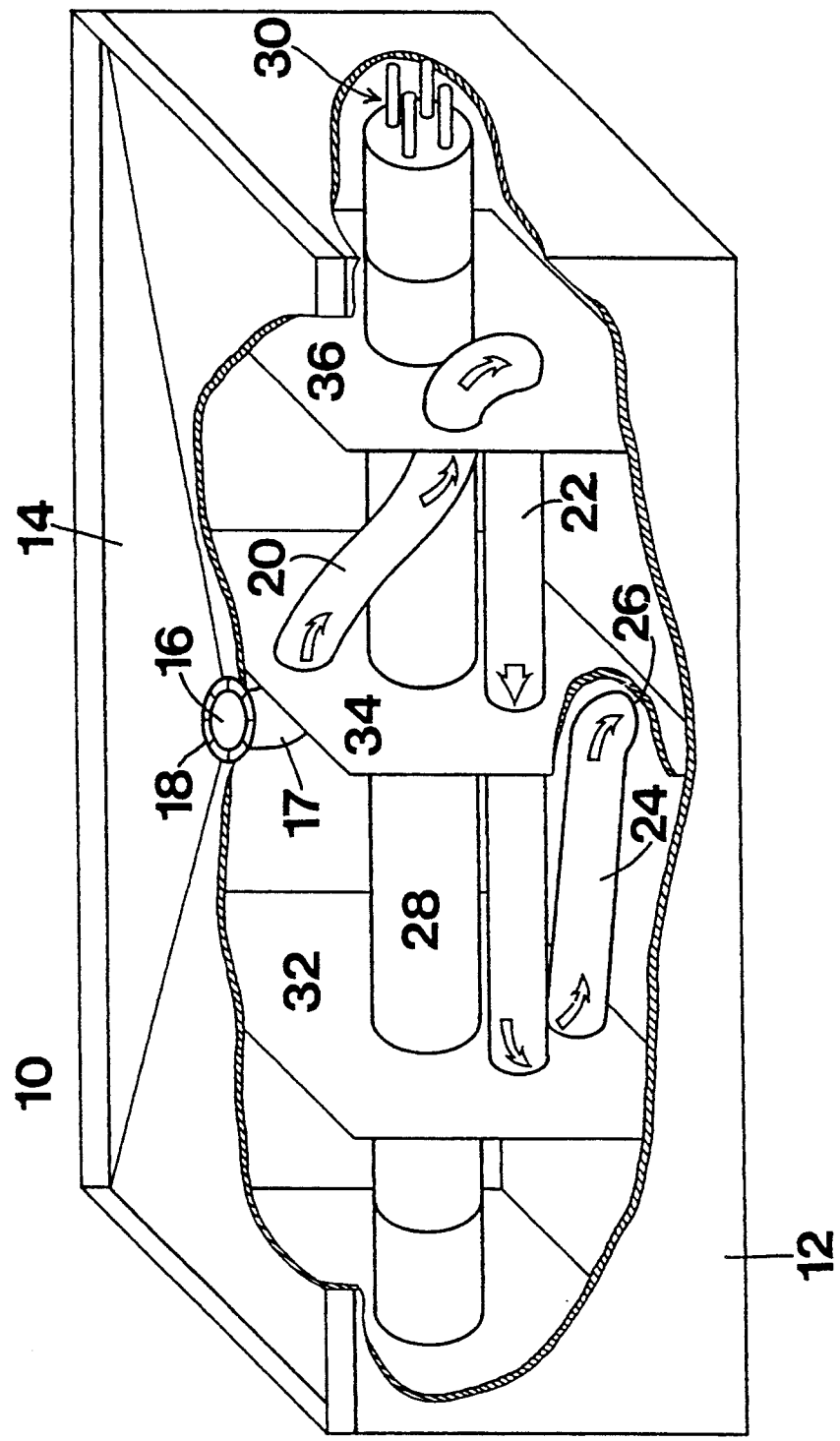
FIG. 1 is an axonometric, partly cross sectional view of an ultraviolet liquid sterilization system of this invention.

There is shown in Fig. 1 an embodiment 10 of the ultraviolet liquid sterilization system of this invention. System 10 includes enclosure 12 housing ultraviolet lamp 28 that has projecting from enclosure 12 electrical lamp connection means 30 as is known in the art. System 10 includes means for gravity feeding a liquid to be sterilized past ultraviolet lamp 28 to expose the liquid to the light to sterilize the liquid. This is accomplished with tube 17 that has inlet 18 at central opening 16 in sloped top 14 of enclosure 12 that acts as a drip tray to collect water thereon and focus it into tube 17. This arrangement allows system 10 to be used to collect and sterilize water dripping from a source such as the evaporator coil of a dehumidifier or an air conditioning unit, for example, so that the water collected may be cleaned and sterilized to make potable water from the air.

Figure 2:
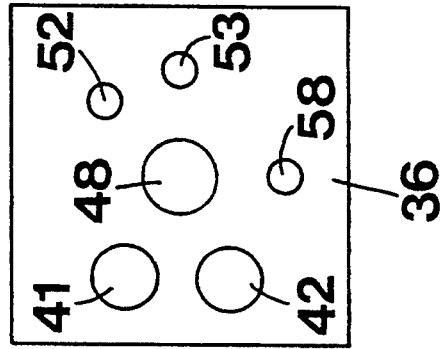
FIG. 2 is a front view of the partitions of the system of FIG. 1 detailing one of many possible schemes for the location of the holes for accomplishing the liquid feed of the system of FIG. 1.
Figure 2:
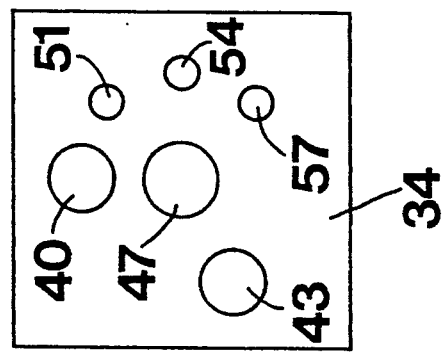
Figure 2:
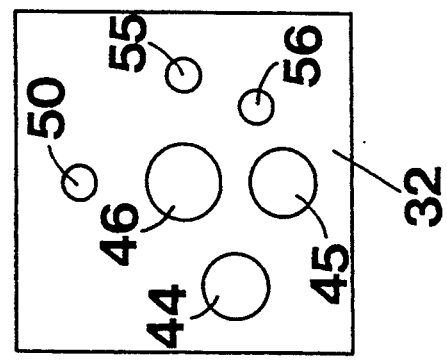

Tube 17 includes first substantially vertical leg or run 20 that passes through enclosure partitions 34 and 36 as is shown in more detail in FIG. 2. Nearly horizontal leg or run 22 of tube 17 provides a long and slow water flow path to increase the residence time so that the water has sufficient ultraviolet light exposure to kill the organisms therein. Such light exposure levels are well known in the art and can be calculated in advance depending on the qualities of the inlet water to provide the means of determining the length of lamp 28 and tube 17, particularly run 22, to provide sufficient exposure. Run 22 passes through partitions 34 and 32 and ends in more vertical outlet run 24 that exits enclosure 12 at exit point 26 through the bottom of enclosure 12. Preferably, both inlet 18 and outlet 26 of tube 17 from enclosure 12 are directly exposed to the light from lamp 28 to provide both a sterile inlet and outlet that prevents live organisms from entering the system from the outside.

FIG. 2 details the arrangement of the holes in partitions 32, 34 and 36, FIG. 1, including the holes that support a second tube for providing a second pass past ultraviolet lamp 28 downstream of the first pass. This second-pass arrangement is typically used when there is a filter(s) included in the system to remove particulates and organics, for example, as is known in the art. Since tile filter requires pressure, in those embodiments with the filter there may be a pump just downstream of outlet 26 to pressurize the water to force it through the filter. In that case, a smaller diameter tube, not shown in Fig. 1 for clarity purposes only, is run through enclosure 12 in a sinuous path that can be more tortuous than the sinuous path of tube 17 because the water is not gravity fed on the second pass. The second pass insures the sterilization of liquid exiting the filtration or treatment system in case there are bacteria or other organisms in the pump, plumbing, and/or filter.

Tube 17 is preferably, but not necessarily, a $\frac{1}{2}''$ diameter convoluted teflon tube that is transmissive to ultraviolet light but can withstand ultraviolet light for long periods of time unlike many other types of UV transmissive plastics. The tubing is preferably convoluted so that it may be bent along the sinuous path shown in FIG. 1. Larger size tubing helps prevent air locks in the tube so that tile liquid can successfully trickle down through the tube past the ultraviolet lamp and be sterilized. On the other hand, the outlet tube may be a smaller diameter non-corrugated teflon tube that is bent to have a number of lengths of tubing parallel to lamp 28 such as shown in FIG. 10 of U.S. Pat. No. 4,479,131. This water flow arrangement may be accomplished, for example, in the embodiment of FIGS. 1 and 2 by including $\frac{1}{2}''$ holes 40 through 45 for allowing $\frac{1}{2}''$ tube 17 to pass therethrough for support of the tube. $\frac{3}{4}''$ holes 46 through 48 in the center of the partitions are included to support lamp 28. $\frac{1}{4}''$, or smaller, holes 50 through 58 provide support for the $\frac{1}{4}''$, or smaller, outlet side tube that, as can be seen from the pattern of holes, makes multiple passes by the ultraviolet lamp.

An alternative embodiment 80, FIG. 3, does not include such teflon tubing, and also may include the ability to accept and sterilize gravity feed water in two passes past the ultraviolet lamp, one before and one after the filter. Embodiment 80 includes enclosure 82 that may or may not have top 84 that, in the same manner as the embodiment of FIG. 1, includes a sloped top leading to opening 86 that acts as the entrance point of water into the sterilization system. As before, opening 86 is exposed to the ultraviolet light to maintain a sterile opening. In this case, enclosure 82 is a rectangular liquid-tight box having a number of partitions/baffle plates 90 through 98 therein that are each sealed to the sides and bottom of enclosure 82 to form a number of adjacent liquid-tight chambers. Partitions 90 through 98, as will become apparent below, are arranged so that they become a series of baffle plates for creating a tortuous liquid flow path past the lamp to increase the liquid light exposure time for greater sterility.

Because enclosure 82 becomes virtually filled with liquid, the ultraviolet lamp must be protected from liquid exposure with water tight quartz housing 88 that passes centrally through each of the baffle plates and is able to accept an ultraviolet lamp, not shown in the drawing. The liquid entering tile enclosure through opening 86 enters the first chamber created between baffle plates 90 and 94. Hole 100 at or near the bottom edge of plate 90 puts this chamber in fluid communication with the second in the series of chambers formed between plates 90 and 91. Plate 91 has hole 101 at or near its top edge so that the liquid entering through entrance 86 must fill up both of these first two chambers before it flows out into the third chamber between plates 91 and 92. Once these first two chambers are filled, any more liquid entering must slowly flow down through the first chamber, through hole 100, and then up through the second chamber and out through hole 101 to create a long liquid residence time that also moves the liquid directly past the ultraviolet light source to ensure sterilization. There is a similar arrangement in the third and fourth chambers formed between plates 91 and 92, and 92 and 93, respectively, to further increase residence time. The final chamber in this first pass is formed between baffle plate 93 and the end wall of enclosure 82. Pump 108 may be placed in this chamber, or outside of the chamber, and accepts water through outlet 109 and pumps it out through tube 110 either to additional filtration or treatment or to storage or to an outlet, as desired depending on the application. Pump 108 may be a float operated or liquid sensing pump so that it operates only when liquid is available to be pumped.

This arrangement allows the use of other materials that can be formed into enclosure 82 and baffle plates 90 through 93 for creating the tortuous liquid flow path. The insides of enclosure 82 may be made UV reflective using proper materials or coatings to increase the ultraviolet treatment of the liquid therein and to protect enclosure 82 if its material is otherwise susceptible to ultraviolet exposure.

System 80 also illustrates a second pass past the ultraviolet lamp using the same type of baffled water flow arrangement illustrated in conjunction with the first pass. The second pass is accomplished with a number of chambers formed between plates 94 and 98 and the end wall 99 of enclosure 82 to create multiple liquid flow chambers in which the liquid flows first through inlet hole 112 and then holes 114, 116, 118, 120 and outlet 122 that is exposed directly to the lamp to create a sterile outlet from the system.

In one embodiment, system 80 includes a box approximately 3¼" on a side and about 16" long to accept a 14" ultraviolet lamp. System 80 may vary in the number of chambers as may be required or desired.

Although specific features of tile invention are shown in some drawings and not others, this is for convenience only as some feature may be combined with any or all of the other features in accordance with the invention. For example, other gravity fed flow arrangements are contemplated within tile scope of this invention.

Other embodiments will occur to those skilled in tile art and are within the following claims:

What is claimed is:

1. An ultraviolet liquid sterilization system, comprising:

a liquid tight enclosure having a bottom, top, and plurality of sides there between, said top being sloped inward towards and opening to drain liquid into said liquid-tight enclosure a series of spaced baffle plates in said liquid tight enclosure dividing said liquid tight enclosure into a first series of adjacent, liquid tight chambers, said series of spaced baffle plates each including an opening;

an ultraviolet lamp supported within the baffle plate openings;

an opening through the lower side of said baffle plate adjacent a first liquid chamber of said first series of adjacent, liquid tight chambers to allow the first liquid tight chamber and a second chambers liquid tight chamber to fill, and to pass liquid from the first liquid tight chamber to the second chamber tight chambers, and an opening through the upper side of said baffle plate adjacent the second liquid tight chamber to pass liquid out of the second liquid tight chamber, said series of spaced baffle plates and openings creating a tortuous liquid flow path past said ultraviolet lamp to increase the liquid's light exposure time for greater sterility.

2. The ultraviolet liquid sterilization system of claim 1 further including a pump in the last, liquid tight chamber of adjacent, liquid tight the first series of chambers for pumping liquid from the last, liquid tight chamber.

3. The ultraviolet liquid sterilization system of claim 2 further including a liquid filter fluidly connected downstream of said pump.

4. The ultraviolet liquid sterilization system of claim 3 in which said liquid tight enclosure includes a second series of adjacent, liquid tight chambers for feeding the liquid past said ultraviolet lamp a second time.

5. The ultraviolet liquid sterilization system of claim 4 in which said second series of adjacent, liquid tight chambers is formed by baffle plates, said baffle plates including openings arranged toward opposite edges of adjacent plates to create a tortuous liquid flow path past the ultraviolet lamp.

6. The ultraviolet liquid sterilization system of claim 5 further including means for directing liquid from said liquid filter to said second series of adjacent, liquid tight chambers.

7. The ultraviolet liquid sterilization system of claim 1 in which inside surfaces of said liquid tight enclosure have an ultraviolet reflective coating.

8. The ultraviolet liquid sterilization system of claim 1 in which inside surfaces of said liquid tight enclosure have an ultraviolet protective coating.

* * * * *